United States Patent
Coffy et al.

(10) Patent No.: US 7,067,451 B1
(45) Date of Patent: Jun. 27, 2006

(54) SOLUBLE MAGNESIUM COMPLEXES USEFUL FOR THE PRODUCTION OF POLYOLEFIN CATALYSTS AND CATALYSTS PREPARED THEREWITH

(75) Inventors: Tim J. Coffy, Houston, TX (US); Steven D. Gray, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 11/016,104

(22) Filed: Dec. 17, 2004

(51) Int. Cl.
*B01J 31/00* (2006.01)

(52) U.S. Cl. ............ 502/150; 502/102; 502/103; 502/104; 502/117; 526/119

(58) Field of Classification Search ........ 502/150, 502/103, 104, 117; 526/119
See application file for complete search history.

(56) References Cited

U.S. PATENT DOCUMENTS

| | | | | |
|---|---|---|---|---|
| 4,107,413 A | | 8/1978 | Giannini et al. | 526/114 |
| 4,114,319 A | | 9/1978 | Governale | 49/488 |
| 4,220,554 A | | 9/1980 | Scata et al. | 252/429 B |
| 4,294,721 A | | 10/1981 | Cecchin et al. | 252/429 B |
| 4,354,959 A | * | 10/1982 | Epstein et al. | 502/105 |
| 4,439,540 A | | 3/1984 | Cecchin et al. | 502/125 |
| 4,460,701 A | | 7/1984 | Terano et al. | 502/104 |
| 4,562,173 A | | 12/1985 | Terano et al. | 502/127 |
| 5,066,738 A | | 11/1991 | Ewen | 526/124 |
| 5,565,245 A | * | 10/1996 | Sun et al. | 427/430.1 |
| 5,614,596 A | * | 3/1997 | Laine et al. | 525/389 |
| 5,698,761 A | * | 12/1997 | Pohl et al. | 585/646 |
| 6,468,550 B1 | * | 10/2002 | Remy | 424/401 |
| 6,472,342 B1 | * | 10/2002 | Agapiou et al. | 502/170 |
| 6,555,640 B1 | * | 4/2003 | Ito et al. | 526/207 |
| 6,693,058 B1 | | 2/2004 | Gray et al. | 502/103 |
| 6,869,904 B1 | * | 3/2005 | Boussie et al. | 502/171 |
| 2001/0051697 A1 | * | 12/2001 | Morse | 526/119 |

* cited by examiner

*Primary Examiner*—J. A. Lorengo
*Assistant Examiner*—Jennine Brown
(74) *Attorney, Agent, or Firm*—Madan, Mossman & Sriram, P.C.

(57) ABSTRACT

A method of forming a polyolefin catalyst component includes halogenating metal complexes. The metal complexes result from reacting a metal alkoxide with an alcohol-ether. A particular non-limiting example is a magnesium complex formed by reacting magnesium alkoxide with an ethylene alcohol-ether, and then chlorinating the magnesium complex. Catalyst components, catalysts, catalyst systems, polyolefin polymers and methods of making each are disclosed.

27 Claims, No Drawings

SOLUBLE MAGNESIUM COMPLEXES USEFUL FOR THE PRODUCTION OF POLYOLEFIN CATALYSTS AND CATALYSTS PREPARED THEREWITH

FIELD OF THE INVENTION

The invention relates to catalysts, methods of making catalysts, and processes for polymerizing olefins, and relates more particularly to polyolefin catalysts, methods of making polyolefin catalysts, and methods of polymerizing olefins.

BACKGROUND OF THE INVENTION

Olefins, also called alkenes, are unsaturated hydrocarbons whose molecules contain one or more pairs of carbon atoms linked together by a double bond. When subjected to a polymerization process, olefins are converted to polyolefins, such as polyethylene and polypropylene. Ziegler-type polyolefin catalysts, their general methods of making, and subsequent use, are known in the polymerization art. While much is known about Ziegler-type catalysts, there is a constant search for improvements in their polymer yield, catalyst life, catalyst activity, amenability to use in large scale production processes, and in their ability to produce polyolefins having certain properties.

Conventional Ziegler-Natta catalysts comprise a transition metal compound generally represented by the formula:

$$MR^+_x$$

where M is a transition metal, $R^+$ is a halogen or a hydrocarboxyl, and x is the valence of the transition metal. Typically, M is a group IVB metal such as titanium, chromium, or vanadium, and $R^+$ is chlorine, bromine, or an alkoxy group. The transition metal compound is typically supported on an inert solid, e.g., magnesium chloride.

The properties of the polymerization catalyst may affect the properties of the polymer formed using the catalyst. For example, polymer morphology typically depends upon catalyst morphology. Acceptable polymer morphology differs for each class of production process (e.g., slurry loop, bimodal, gas phase, etc.), but typically includes uniformity of particle size and shape and an acceptable bulk density. Furthermore, there is a need in the art of preparing polymers to minimize the number of very small polymer particles (i.e., fines) to avoid plugging polymer transfer lines or solvent recovery systems.

SUMMARY OF THE INVENTION

In one aspect, the invention is a process for making a catalyst precursor that involves contacting a metal compound of the formula $M(OR)_2$ with alcohol-ethers of the formula $HOCR^1R^2CR^3R^4OR^5$ to form a three- or four-coordinate catalyst precursor having the general formula:

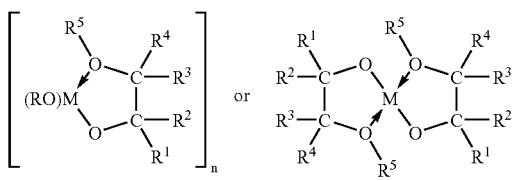

where M is a metal from Group IIA of the Periodic Table, n=1 or 2, R is a hydrocarbyl having from 1 to 20 carbon atoms; $R^1$, $R^2$, $R^3$, $R^4$ and $R^5$ are the same or different; and $R^1$, $R^2$, $R^3$, $R^4$ and $R^5$ are a substituted or unsubstituted alkyl or aryl moiety having from about 1 to about 20 carbons atoms or hydrogen. In one specific, non-limiting embodiment of the invention M is magnesium and R is ethyl.

In another aspect, the invention is a process for olefin polymerization, the process including contacting one or more olefin monomers together in the presence of a catalyst under polymerization conditions, wherein the catalyst is produced by a process including contacting a metal compound of the formula $M(OR)_2$ with alcohol-ethers of the formula $HOCR^1R^2CR^3R^4OR^5$ to form a three- or four-coordinate catalyst precursor having the general formula:

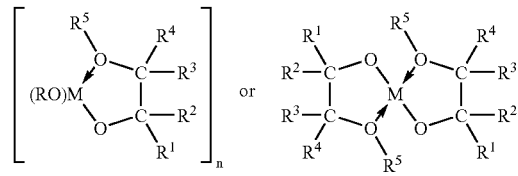

where M is a metal from Group IIA of the Periodic Table, n=1 or 2, R is a hydrocarbyl having from 1 to 20 carbon atoms; $R^1$, $R^2$, $R^3$, $R^4$ and $R^5$ are the same or different; and $R^1$, $R^2$, $R^3$, $R^4$ and $R^5$ are a substituted or unsubstituted alkyl or aryl moiety having from about 1 to about 20 carbons atoms or hydrogen.

Another aspect of the invention is a catalyst produced by a process contacting a metal compound of the formula $M(OR)_2$ with alcohol-ethers of the formula $HOCR^1R^2CR^3R^4OR^5$ to form a three- or four-coordinate catalyst precursor having the general formula:

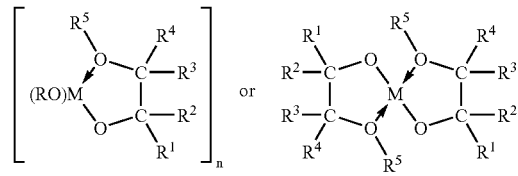

where M is a metal from Group IIA of the Periodic Table, n=1 or 2, R is a hydrocarbyl having from 1 to 20 carbon atoms; $R^1$, $R^2$, $R^3$, $R^4$ and $R^5$ are the same or different; and $R^1$, $R^2$, $R^3$, $R^4$ and $R^5$ are a substituted or unsubstituted alkyl or aryl moiety having from about 1 to about 20 carbons atoms or hydrogen.

An aspect of the invention is a polymer produced by a process including contacting one or more olefin monomers in the presence of a catalyst, the catalyst being produced by a process including contacting a metal compound of the formula $M(OR)_2$ with alcohol-ethers of the formula $HOCR^1R^2CR^3R^4OR^5$ to form a three- or four-coordinate catalyst precursor having the general formula:

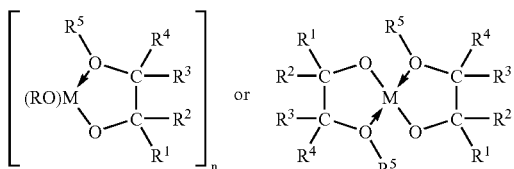

where M is a metal from Group IIA of the Periodic Table, n=1 or 2, R is a hydrocarbyl having from 1 to 20 carbon atoms; $R^1$, $R^2$, $R^3$, $R^4$ and $R^5$ are the same or different; and $R^1$, $R^2$, $R^3$, $R^4$ and $R^5$ are a substituted or unsubstituted alkyl or aryl moiety having from about 1 to about 20 carbons atoms or hydrogen.

In still another aspect, the invention is an article of manufacture including an article prepared using a polymer produced by a process including contacting one or more olefin monomers in the presence of a catalyst, the catalyst being produced by a process including contacting a metal compound of the formula $M(OR)_2$ with alcohol-ethers of the formula $HOCR^1R^2CR^3R^4OR^5$ to form a three- or four-coordinate catalyst precursor having the general formula:

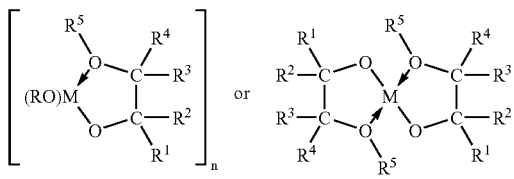

where M is a metal from Group IIA of the Periodic Table, n=1 or 2, R is a hydrocarbyl having from 1 to 20 carbon atoms; $R^1$, $R^2$, $R^3$, $R^4$ and $R^5$ are the same or different; and $R^1$, $R^2$, $R^3$, $R^4$ and $R^5$ are a substituted or unsubstituted alkyl or aryl moiety having from about 1 to about 20 carbons atoms or hydrogen. The polymer may be formed into a film and employed in food packaging; the polymer may be formed by blow molding and the blown molded article may be a milk bottle, bleach bottle or a toy part; or the polymer may be formed into pipe and the article is a PE 100 pressure-rated pipe.

DETAILED DESCRIPTION OF THE INVENTION

One commonly used polymerization process involves contacting an olefin monomer with a catalyst system that includes a conventional Ziegler-Natta catalyst, a co-catalyst, and one or more electron donors. Examples of such catalyst systems are provided in U.S. Pat. Nos. 4,107,413; 4,294,721; 4,439,540; 4,114,319; 4,220,554; 4,460,701; 4,562,173; and 5,066,738, which are incorporated herein by reference.

The invention relates to the production of novel, three or four coordinate, metal complexes as precursors for Ziegler-Natta catalysts, in one non-restrictive version magnesium catalysts. The discovery of new magnesium complexes with high solubility in hydrocarbon solvents is important to the development of Ziegler-Natta catalysts and was not predicted.

It has been surprisingly and unexpectedly discovered that magnesium complexes of the general class, $Mg(OCH_2CH_2OR)_2$ are readily generated in situ by the reaction of $Mg(OEt)_2$ and ethylene alcohol-ethers as shown below:

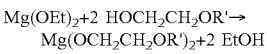

$Mg(OEt)_2 + 2\ HOCH_2CH_2OR' \rightarrow Mg(OCH_2CH_2OR')_2 + 2\ EtOH$

These above-mentioned complexes are soluble in hydrocarbon solvents such as heptane and toluene. The central metal or magnesium core in these complexes can be be four coordinate. In an alternative embodiment, one equivalent of the ethylene alcohol-ether can be used to produce a 3 coordinate catalyst precursor. The steric bulk afforded by these ligands allows their conversion to magnesium chloride-supported Ziegler-Natta catalysts by treatment with titanium chlorides of the general class $Ti(OR)_zCl_{4-z}$ (where z=0–4) to occur in a very controlled fashion. This feature is important to the development of catalysts capable of providing polyolefins with a controlled morphology.

The catalyst precursor components of the invention have the general type of formula:

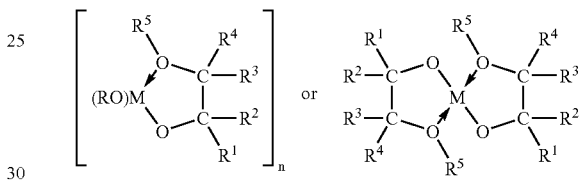

where M is a metal from Group IIA of the Periodic Table, n=1 or 2, R is a hydrocarbyl having from 1 to 20 carbon atoms; $R^1$, $R^2$, $R^3$, $R^4$ and $R^5$ are the same or different; and $R^1$, $R^2$, $R^3$, $R^4$ and $R^5$ are a substituted or unsubstituted alkyl or aryl moiety having from about 1 to about 20 carbons atoms or hydrogen. Substituted alkyl radicals such as —$CF_3$, —$CCl_3$, and the like; radicals including Si and silicon ethers such as —O—$SiO_2$; and aryl radicals such as a nitrobenzyl radical and an anisole radical may be used.

Suitable metal alkoxides may generally be described as having two alkoxide groups. The alkoxide groups may each be independently selected from among unsubstituted and substituted alkoxides having alkyl groups in the range of 1 to 10 carbons atoms. In one embodiment, the alkoxide groups have 1 to 4 carbon atoms, such as 2 to about 4 carbons atoms. Non-limiting examples of metal alkoxides suitable for use include magnesium alkoxides such as, for example, magnesium ethoxide.

A wide variety of alcohol-ethers are available both commercially and via the treatment of epoxides with alcohols and amines which afford the opportunity to "fine tune" both the steric and the electronic properties of the magnesium complex. Specific examples of suitable alcohol-ethers include, but are not necessarily limited to: ethylene glycol monopropyl ether, ethylene glycol monoethyl ether, ethylene glycol monobutyl ether, propylene glycol monomethyl ether, and the like.

In the invention, suitable metal alkoxides may generally be described as having two alkoxide groups. The alkoxide groups can each be independently selected from among unsubstituted and substituted alkoxides having alkyl groups in the range of 1 to 10 carbons atoms. In another non-limiting embodiment of the invention, the alkoxide groups have 1 to 4 carbon atoms, such as 2 to about 4 carbons atoms. Non-limiting examples of metal alkoxides suitable for use in the invention include, but are not necessarily limited to, magnesium alkoxides such as, for example, magnesium ethoxide.

In the practice of forming the catalyst components of the invention, the metal alkoxide is generally contacted with the alkylene alcohol-ether at conditions suitable to yield the desired metal catalyst precursor complex. Suitable temperatures for the contacting of the metal alkoxide with the alkylene alcohol-ether are generally in the range of about −20° C. to about 100° C., desirably in the range of about 0° C. to about 50° C., and may be in the range of about 0° C. to about 25° C. The slurry may be heated to facilitate displacement substitution of the OR group with the alkylene alcohol-ether. In the practice of the invention, the metal alkoxide and alkylene alcohol-ether may be contacted together in any suitable solvent or reaction medium. Non-limiting examples of suitable solvents or reaction media include toluene, heptane, hexane, octane and the like.

The catalyst precursor may be further modified by contacting the precursor with an organometallic agent. Suitable organometallic agents include but are not limited to aluminum alkyls, aluminum alkyl hydrides, lithium aluminum alkyls, zinc alkyls, magnesium alkyls and the like. Contacting the precursor with the organometallic agents may reduce solution viscosity and may also reduce byproducts such as alcohols.

The catalyst precursor may be halogenated to form a catalyst support. It may also be titanated or titanated and halogenated to form a supported catalyst. Agents useful for halogenating the metal bis(alkylene alcohol-ether) include any halogenating agent which, when utilized in the invention, will yield a suitable catalyst. Some of the halogenating agents may also serve as titanating agents useful for incorporating titanium into the catalyst precursor which is necessary to impart catalytic properties to the catalysts precursor. For example, $TiCl_4$ may both titanate and halogenate a catalyst precursor.

Metal chlorides may be desirable halogenating agents and/or titanating/halogenating agents. Non-limiting examples of suitable halogenating and/or titanating/halogenating agents include Group III, Group IV and Group V halides, hydrogen halides, or the halogens themselves. Specific examples of halogenating and/or titanating/halogenating agents are $BCl_3$, $AlCl_3$, $CCl_4$, $SiCl_4$, $TiCl_4$, $ZrCl_4$, $VOCl_4$, $VOCl_2$, $CrOCl_2$, $SbCl_5$, $POCl_2$, $PCl_5$, $HfCl_4$, and $Ti(OR)_nCl_{4-n}$, wherein R is an alkyl having 1 to 8 carbon atoms, and n is from 0 to 4. Mixtures of any of two or more of the foregoing may also be used as halogenating and/or titanating/halogenating agents. Other halogenating and/or titanating/halogenating agents include alkyl halo silanes of the formula $R'_nSiX_{(4-n)}$, wherein X is a halogen, R' is a substituted or unsubstituted hydrocarbyl having 1 to 20 carbon atoms, and n is 1–3

Possible halogenating and/or titanating/halogenating agents are $SiCl_4$, $TiCl_4$, $TiCl_n(OR)_{4-n}$, and mixtures of any of two or more of the foregoing. One embodiment employs as the halogenating agent a mixture of $TiCl_4$, and $Ti(OR)_4$, wherein R is a butyl group. The molar ratio of $TiCl_4$ to $Ti(OR)_n$ is generally in the range of about 4 to about 0.1, may be in the range of about 3 to about 1, and may be in the narrower range of about 2 to about 1.

In the practice of the invention, there is generally at least one halogenation step, and there may be two or more. A non-limiting example of a suitable halogenation treatment includes a first halogenation treatment with a mixture of $TiCl_4$ and $Ti(OR)_4$, followed by a second halogenation treatment with $TiCl_4$. Halogenation and titanation of catalysts and catalyst precursors is disclosed in U.S. Pat. No. 6,693,058 to Coffy, et al., the contents of which are incorporated herein by reference.

The halogenation and titanation of the metal bis(alkylene alcohol-ether) may be carried out under conditions suitable to yield the desired catalyst component. Suitable temperatures for halogenating and titanating are generally in the range of about −20° C. to about 100° C., may be in the range of about 0° C. to about 75° C. and may be in the narrower range of about 25° C. to about 65° C.

In the practice of the invention, halogenation may be conducted at a molar ratio of halogenating agent to metal bis(alkylene alcohol-ether) generally in the range of about 1 to about 20, may be in the range of about 1 to about 10, and may be in the narrower range of about 1 to about 8.

In the practice of the invention, the halogenating agent and the metal bis(alkylene alcohol-ether) may be contacted together in any suitable solvent or reaction medium. Non-limiting examples of suitable solvents or reaction media include toluene, heptane, hexane, octane and the like.

In contrast to conventional practice, in an embodiment of the invention, a solid product precipitated in the halogenation and/or titanation step is the desired catalyst or support component that is then recovered by any suitable recovery technique. This desired catalyst or support component may then be utilized as a catalyst for the production of a controlled morphology Ziegler-Natta-type catalyst. The catalyst can be formed by direct precipitation of the three- or four-coordinate soluble intermediate, or it can be precipitated in the presence of a support template to form a supported catalyst. Silica or magnesium chloride can be used as a support template.

An internal electron donor for treating the catalyst or catalyst precursor may be used. The internal electron donor may be added during or after the halogenation step. Internal electron donors for use in the preparation of polyolefin catalysts are known, and any suitable internal electron donor may be utilized in the invention that will provide a suitable catalyst. Internal electron donors, also known as Lewis bases, are organic compounds of oxygen, nitrogen, phosphorous, or sulfur which are capable of donating an electron pair to the catalyst. The internal electron donor may be a monofunctional or polyfunctional compound, and may be selected from among the aliphatic or aromatic carboxylic acids and their alkyl esters, the aliphatic or cyclic ethers, ketones, vinyl esters, acryl derivatives, particularly alkyl acrylates or methacrylates and silanes. The amount of internal electron donor utilized may vary over a broad range and is generally in the range of about 0.01 to about 2 equivalents, but may be in the range of about 0.05 to about 0.5 equivalents. The catalyst precursor may be contacted with the internal electron donor for a contacting period in the range of about 0.5 hours to about 4 hours. In one embodiment a range of about 1 hour to about 2 hours is employed.

The catalyst made by the above described process may be combined with an organo-aluminum cocatalyst component to generate a catalyst system suitable for the polymerization of olefins. Typically, the cocatalysts which are used together with the transition metal containing catalyst are organometallic compounds of Group Ia, IIa, and IIIa metals such as aluminum alkyls, zinc alkyls, magnesium alkyls and the like. Organometallic compounds that may be employed in the practice of the invention are trialkylaluminum compounds.

External electron donors that may be added at the end of the preparation or utilized with the use of catalyst during polymerization and include those known in the art, including, but not limited to alkoxysilanes.

The catalysts described herein may be used for the polymerization of olefins, including α-olefins. For example, the present catalyst is useful for catalyzing ethylene, propylene, butylene, pentene, hexene, 4-methylpentene and other alkenes having at least 2 carbon atoms, and also for mixtures thereof. These catalysts may be utilized for the polymerization of ethylene to produce polyethylene, such as polyethylene with controlled powder morphology. Olefin polymerization methods are well known in general, and any suitable method may be utilized. The catalysts of the invention may offer improvements in one or more of the following properties: activity, morphology control, fines reduction, and hydrogen response.

In one embodiment, the polymers of the invention are converted into a film and the film used in food packaging. In another embodiment, the polymer is converted by blow molding and the molded article is a milk bottle, bleach bottle or toy part. In still another embodiment, the polymer is formed into pipe and the pipe is a PE-100 pressure-rated pipe.

The following non-limiting example is provided merely to illustrate the invention, and is not meant to limit the scope of the claims.

EXAMPLE

In a drybox a four-necked, one-liter flask is equipped with a 125 ml addition funnel, a magnetic stir bar, a condenser with a gas inlet, a thermometer, and a septum. The flask is charged with $Mg(OEt)_2$ (2.5 g, 22 mmol) and brought to the Schlenk line where it is placed under a rapid argon purge. Heptane (100 ml) is added to the flask and the mixture is rapidly stirred.

A solution of ethylene glycol monopropyl ether (EPH, 4.58 g, 44 mmol) diluted to 100 ml total volume with heptane is added dropwise to the $Mg(OEt)_2$ slurry. Immediate reaction is seen as the solution grew cloudy. The solution is next heated to reflux. Gradually with heating, the solution became slightly yellow in color and the solid completely dissolved. Upon reaching 78° C., a component of the solution is seen to reflux. Heating is continued until the solution temperature reached 90° C. The mixture is allowed to react at this temperature for 1 hour.

The solution is cooled to 75° C. and a solution of TEAI (1.67 g, 14.7 mmol) in heptane (diluted to 50 ml total volume) is next added dropwise to the slurry. Addition is complete in 45 minutes and the solution is mobile and clear at this time. The mixture is allowed to stir at 55° C. for 30 minutes.

After 1 hour, the solution is allowed to cool to room temperature. No solid formation is seen upon cooling the solution. The solvent is next removed under reduced pressure to yield $Mg(OCH_2CH_2OCH_2CH_2CH_3)_2$ as a yellow gel.

This complex and others of the class are subjected to treatment with titanium chlorides of the general class $TiCl(OR)_{4-z}$ (z=0–4) to provide magnesium chloride supported Ziegler-Natta catalysts for the production of polyolefins.

While the illustrative embodiments of the invention have been described with particularity, it will be understood that various other modifications will be apparent to, and may be readily made by, those skilled in the art without departing from the scope of the invention. Accordingly, it is not intended that the scope of the claims appended hereto be limited to the examples and descriptions set forth herein but rather that the claims be construed as encompassing all the features of patentable novelty which reside in the invention, including all features which would be treated as equivalents thereof by those skilled the art to which this invention pertains.

What is claimed is:

1. A process for making a catalyst precursor comprising contacting a metal compound of the formula $M(OR)_2$ with alcohol-ethers of the formula $HOCR^1R^2CR^3R^4OR^5$ to form a three- or four-coordinate catalyst precursor having the general formula:

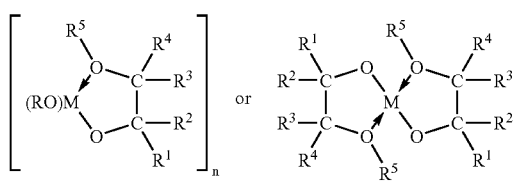

where M is a metal from Group IIA of the Periodic Table, n=1 or 2, R is a hydrocarbyl having from 1 to 20 carbon atoms; $R^1$, $R^2$, $R^3$, $R^4$ and $R^5$ are the same or different; and $R^1$, $R^2$, $R^3$, $R^4$ and $R^5$ are a substituted or unsubstituted alkyl or aryl moiety having from about 1 to about 20 carbons atoms or hydrogen.

2. The process of claim 1 wherein M is magnesium, and wherein R is ethyl.

3. The process of claim 1 wherein the alcohol-ether is ethylene glycol monopropyl ether.

4. The process of claim 1 further comprising contacting the catalyst precursor with an organometallic agent.

5. The process of claim 1 further comprising contacting the catalyst precursor with a first halogenating and/or halogenating/titanating agent to form a halogenated catalyst precursor.

6. The process of claim 5 further comprising contacting the halogenated catalyst precursor with a second halogenating and/or halogenating/titanating agent.

7. The process of claim 1 further comprising contacting the catalyst precursor with a titanating agent to form a catalyst.

8. The process of claim 7 further comprising contacting the catalyst with a halogenating agent.

9. The process of claim 5 wherein the first halogenating and/or halogenating/titanating agent is a mixture of $Ti(OBu)_4$ and $TiCl_4$.

10. The process of claim 6 wherein the second halogenating and/or halogenating/titanating agent is $TiCl_4$.

11. The process of claim 4 wherein the organometallic agent comprises an organo-aluminum compound.

12. The process of claim 4 further comprising adding at least one internal electron donor.

13. The process of claim 4 further comprising precipitating the catalyst with a support template.

14. A process for olefin polymerization, the process comprising contacting one or more olefin monomers together in the presence of a catalyst under polymerization conditions, wherein the catalyst is produced by a process comprising contacting a metal compound of the formula $M(OR)_2$ with alcohol-ethers of the formula $HOCR^1R^2CR^3R^4OR^5$ to form a three- or four-coordinate catalyst precursor having the general formula:

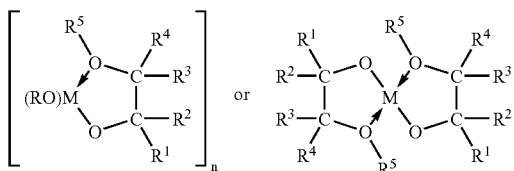

where M is a metal from Group IIA of the Periodic Table, n=1 or 2, R is a hydrocarbyl having from 1 to 20 carbon atoms; $R^1$, $R^2$, $R^3$, $R^4$ and $R^5$ are the same or different; and $R^1$, $R^2$, $R^3$, $R^4$ and $R^5$ are a substituted or unsubstituted alkyl or aryl moiety having from about 1 to about 20 carbons atoms or hydrogen.

15. The process of claim 14 further comprising extracting polyolefin polymers.

16. A catalyst produced by a process comprising contacting a metal compound of the formula $M(OR)_2$ with alcohol-ethers of the formula $HOCR^1R^2CR^3R^4OR^5$ to form a three- or four-coordinate catalyst precursor having the general formula:

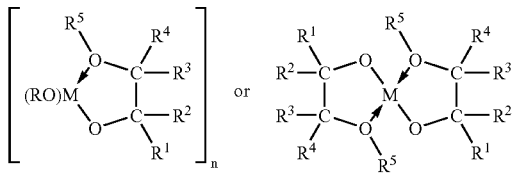

where M is a metal from Group IIA of the Periodic Table, n=1 or 2, R is a hydrocarbyl having from 1 to 20 carbon atoms; $R^1$, $R^2$, $R^3$, $R^4$ and $R^5$ are the same or different; and $R^1$, $R^2$, $R^3$, $R^4$ and $R^5$ are a substituted or unsubstituted alkyl or aryl moiety having from about 1 to about 20 carbons atoms or hydrogen.

17. The catalyst of claim 16 wherein M is magnesium, and wherein R is ethyl.

18. The catalyst of claim 16 where the alcohol-ether is is ethylene glycol monopropyl ether.

19. The catalyst of claim 16 wherein the catalyst precursor is contacted with an organometallic agent.

20. The catalyst of claim 16 wherein the catalyst precursor is contacted with a first halogenating and/or halogenating/titanating agent to form a halogenated catalyst precursor.

21. The catalyst of claim 20 wherein the halogenated catalyst precursor is contacted with a second halogenating and/or halogenating/titanating agent.

22. The catalyst of claim 16 wherein the catalyst precursor is contacted with a titanating agent to form a catalyst component.

23. The catalyst of claim 22 wherein the catalyst component is contacted with a halogenating agent.

24. The catalyst of claim 20 wherein the first halogenating and/or halogenating/titanating agent is a mixture of $Ti(OBu)_4$ and $TiCl_4$.

25. The catalyst of claim 21 wherein the second halogenating and/or halogenating/titanating agent is $TiCl_4$.

26. The catalyst of claim 16 wherein the process further comprises the addition of an internal electron donor.

27. The catalyst of claim 17 wherein the process further comprises precipitating the catalyst in the presence of a support template.

* * * * *